United States Patent [19]

Kelley et al.

[11] Patent Number: 4,524,790
[45] Date of Patent: Jun. 25, 1985

[54] DEVICE FOR CLEANING TEETH AND ORTHODONTAL BRACES

[76] Inventors: Robert E. Kelley, 166 Cross St., Gardner, Mass. 01440; David Prince, 638 Lancaster Rd., Leominster, Mass. 01453

[21] Appl. No.: 535,561

[22] Filed: Sep. 26, 1983

[51] Int. Cl.³ .............................................. A45D 44/18
[52] U.S. Cl. .................................... 132/84 R; 222/79
[58] Field of Search ............. 132/84 R, 1 R, DIG. 4; 222/78, 79; D21/146, 147

[56] References Cited

U.S. PATENT DOCUMENTS

| | | | |
|---|---|---|---|
| 2,793,380 | 5/1957 | Brown et al. | 222/79 |
| 3,091,370 | 5/1963 | Weiner | 222/79 |
| 3,116,855 | 1/1964 | Thomson | 222/79 |
| 3,146,911 | 9/1964 | Shun | 222/79 |
| 3,202,318 | 8/1965 | Black | 222/79 |

*Primary Examiner*—Hugh R. Chamblee
*Assistant Examiner*—Carolyn A. Harrison

[57] ABSTRACT

A pocket or purse dental cleaning device comprising a substantially square shaped housing for containing fluid, and a nozzle, a thumb manipulated actuator for a pump, and a filling opening all in line on an edge of the housing.

1 Claim, 3 Drawing Figures

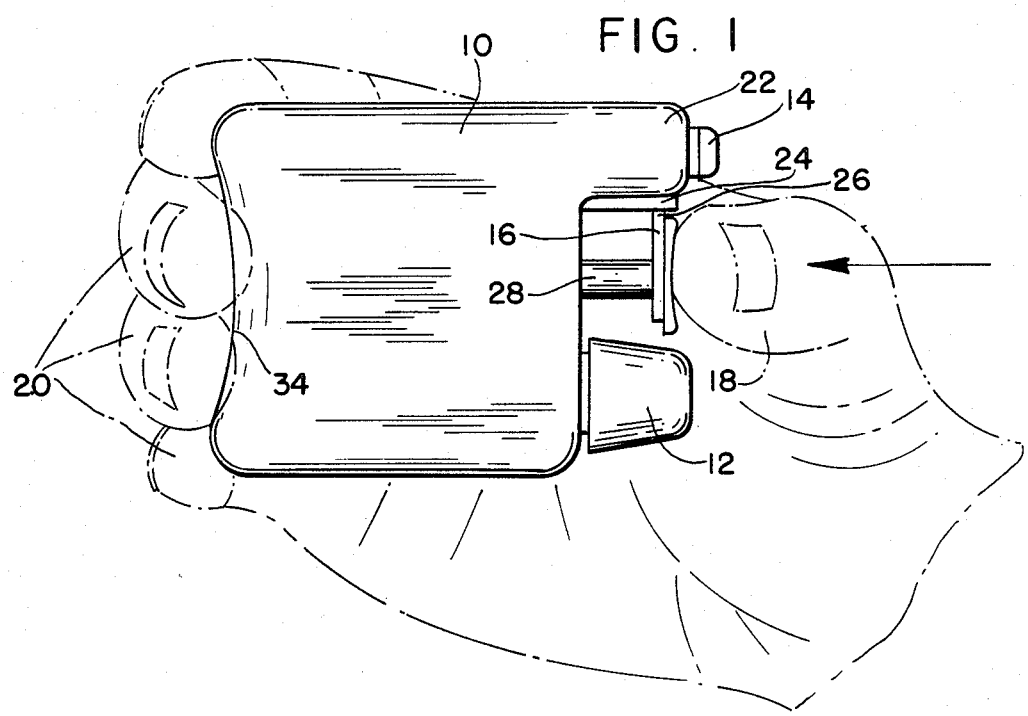
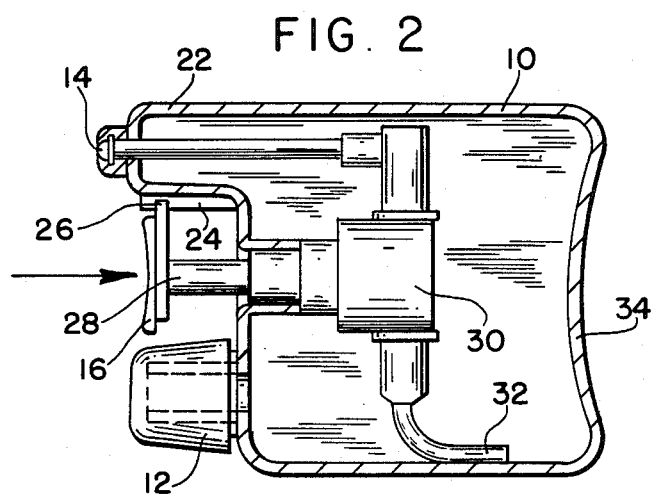
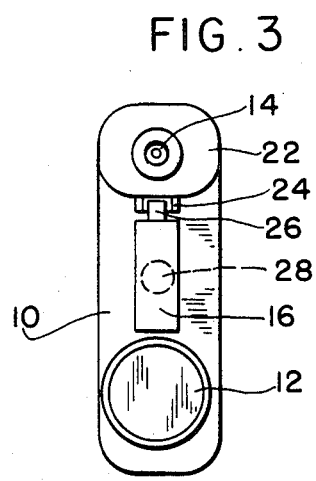

DEVICE FOR CLEANING TEETH AND ORTHODONTAL BRACES

BACKGROUND OF THE INVENTION

Presently, more people, besides children and including teenagers and young and even old adults are undergoing orthodontia even for relatively minor misalignments and malocclusions because the appearance of the teeth is becoming more and more important to the average person. Modern braces are often more apparent, and unsightly food particles are more apparent when stuck between teeth or on the braces and in dentures. It becomes more important to be able to clean out such particles for cosmetic reasons especially in public places where paste or powder and water and brushes are not available. Children are also capable of using this invention, and in fact often find its use in the nature of a game. At the same time, dental hygiene is promoted.

SUMMARY OF THE INVENTION

The present invention is for carrying in pocket or purse and is accessible at all times. It is based on the water pistol concept but greatly differs because it has no pistol grip or barrel. It is made of a kind of square reservoir having a filling opening, a thumb operated depressible actuator, and an exit nozzle aligned in a row on one edge of a substantially square housing mounting the thumb operated pump and acting as a reservoir for fluid to be projected in a stream at the teeth. The nozzle is held adjacent the teeth, brace, etc. and with a natural thumb operation, a stream of cleaning water is projected at the area to be processed. Often, the particles to be dislodged are felt as by the tongue, and no mirror is needed.

The cleaning fluid may be of any appropriate kind: colored, flavored, or of mouthwash type, sweetening the breath. The shape of the device is such as to make it difficult to use as a water pistol, but very easy to use as a tooth cleaner.

BRIEF DESCRIPTION OF THE DRAWINGS

FIG. 1 is a side elevational view;

FIG. 2 is a vertical sectional view; and

FIG. 3 is a front elevational view with part in section, showing the invention.

PREFERRED EMBODIMENTS OF THE INVENTION

The housing 10 may be molded in two parts which are edge cemented together, or in any other manner that is feasible. It is generally square and impervious at sides, top, bottom, and rear edge. At the front edge it has a filling aperature and cap 12; a nozzle 14, and a thumb piece 16 adapted to be pressed in the direction of the arrows in FIGS. 1 and 2, by the thumb 18 of the right (or left) hand, the other fingers of this hand being indicated at 20, gripping the housing.

The housing is hollow to accommodate an amount of the water or fluid to be used to clean the teeth, the fluid entering the filling aperture closed by cap 12.

The numeral 16 indicates the thumb piece by which to operate the device, and which is located midway between the filling aperture cap 12 and the nozzle 14. The thumb piece does not extend out past the filling cap and nozzle which act to protect it to prevent accidental operation in the user's pocket or purse. The nozzle is mounted on a rounded hollow projection 22, which is part of the housing and the cap 12, also being rounded, provides for a harmonious outline, the device having no barrel or pistol grip. At the lower portion of the projection 22, there is an open bottom slot 24 slideably receiving a tit 26 on the thumb piece in order to prevent turning of the thumb piece out of protective position, See FIGS. 1 and 3.

The thumb piece is secured to a piston 28 operating a pump 30 to force fluid therethrough from an intake 32 to the nozzle. The pump and pertinent parts are commercial and obtainable at many supply houses.

In use, the nozzle is placed to play directly on a tooth or braces that have received and retained some kind of particle that is desired to be removed, and upon actuation of the thumb piece, a jet will cleanse the same. Little power is needed to remove such particles, and it will be seen that food particles are easily flushed from the teeth or braces. The size of the housing is generally adapted to the size of the hand just slightly smaller than a pack of cigarettes and the convex shape of the housing at the rear edge 34 accommodates the fingers for best manual gripping of the device. While it is best to operate the cleaning device in conjunction with a mirror, this is not always necessary. Even children can successfully use the device and enjoy doing so especially when agreeable flavors are used in the fluid. The shape of the device does not lend itself to use as a water pistol because of its compactness and lack of a pistol grip, so that its use as intended is to be expected rather than as a plaything.

We claim:

1. A device for cleaning particles of food from teeth or orthodonture devices comprising a generally flat hollow housing adapted to contain fluid material, said housing being substantially square shaped and including two rigid walls with four contiguous edges, three of said edges all being completely closed, the fourth edge mounting a nozzle for a pump and a thumb manipulated operator for the pump which extend outwardly of the housing, and a filling opening and a filling cap, said nozzle, cap and operator being located closely together in a single line with the thumb manipulated operator between the nozzle and the filling cap, said filling cap, operator, and nozzle all extending from the housing at a single edge thereof approximately equally so that their outermost ends are substantially flush so that some of the fingers can engage the opposite edge of the housing to hold it and the user's thumb can operate the pump operator.

* * * * *